(12) United States Patent
Brouet et al.

(10) Patent No.: US 11,260,167 B2
(45) Date of Patent: Mar. 1, 2022

(54) AUTOMATIC FLUID PRODUCT INJECTION DEVICE

(71) Applicant: APTAR FRANCE SAS, Le Neubourg (FR)

(72) Inventors: Guillaume Brouet, Rouen (FR); Sam Reeves, Bristol (GB)

(73) Assignee: APTAR FRANCE SAS, Le Neubourg (FR)

( * ) Notice: Subject to any disclaimer, the term of this patent is extended or adjusted under 35 U.S.C. 154(b) by 365 days.

(21) Appl. No.: 16/486,912

(22) PCT Filed: Feb. 16, 2018

(86) PCT No.: PCT/FR2018/050375
§ 371 (c)(1),
(2) Date: Aug. 19, 2019

(87) PCT Pub. No.: WO2018/150147
PCT Pub. Date: Aug. 23, 2018

(65) Prior Publication Data
US 2020/0009315 A1    Jan. 9, 2020

(30) Foreign Application Priority Data
Feb. 20, 2017 (FR) ...................... 1751321

(51) Int. Cl.
*A61M 5/14* (2006.01)
*A61M 5/142* (2006.01)
(Continued)

(52) U.S. Cl.
CPC ........ *A61M 5/1408* (2013.01); *A61M 5/1422* (2013.01); *A61M 5/14248* (2013.01);
(Continued)

(58) Field of Classification Search
CPC .... A61M 2005/005; A61M 2005/1402; A61M 2005/1403; A61M 5/1407; A61M 5/1408;
(Continued)

(56) References Cited

U.S. PATENT DOCUMENTS

| | | | | |
|---|---|---|---|---|
| 4,515,584 A | * | 5/1985 | Abe | ..................... A61M 5/1723 |
| | | | | 417/477.1 |
| 5,505,704 A | * | 4/1996 | Pawelka | ................. A61M 5/19 |
| | | | | 604/191 |

(Continued)

FOREIGN PATENT DOCUMENTS

| | | |
|---|---|---|
| EP | 2 179 754 A1 | 4/2010 |
| EP | 2 736 565 A2 | 6/2014 |

(Continued)

OTHER PUBLICATIONS

Translation of International Preliminary Report on Patentability, dated Apr. 9, 2019 from the International Bureau in counterpart International application No. PCT/FR2018/050375.

(Continued)

*Primary Examiner* — Quynh-Nhu H. Vu
(74) *Attorney, Agent, or Firm* — Sughrue Mion, PLLC

(57) ABSTRACT

An automatic fluid injection device comprising: a base body (1) for coming into contact with an injection zone; a support assembly (2) for supporting an actuator mechanism (5, 6, 7) that is controlled by power supply means (11); at least one fluid reservoir (3), each containing an injection piston (35), arranged in said base body (1); a needle assembly (100) comprising an insertion actuator (8), needle movement means (9, 9'), a priming needle (101) for associating with each reservoir (3) and for penetrating into said reservoir (3) before moving its piston (35), and an injection needle (102) for penetrating into the injection zone and for injecting the contents of said reservoir(s) (3) into said injection zone, said device including at least one actuator button (200) for (Continued)

priming, inserting the injection needle into the injection zone, administering fluid, and then retracting the injection needle.

18 Claims, 5 Drawing Sheets

(51) Int. Cl.
 *A61M 5/162* (2006.01)
 *A61M 5/145* (2006.01)
(52) U.S. Cl.
 CPC ........ *A61M 5/14546* (2013.01); *A61M 5/162* (2013.01); *A61M 2005/1402* (2013.01); *A61M 2005/14252* (2013.01); *A61M 2205/8206* (2013.01)
(58) Field of Classification Search
 CPC ...... A61M 2005/14252; A61M 5/1422; A61M 5/14248; A61M 5/14546; A61M 5/162; A61M 5/19
 See application file for complete search history.

(56) References Cited

U.S. PATENT DOCUMENTS

| | | | | |
|---|---|---|---|---|
| 9,220,835 | B2* | 12/2015 | Cane' | A61M 5/1422 |
| 2002/0049415 | A1* | 4/2002 | Fukuda | A61M 5/1456 |
| | | | | 604/191 |
| 2007/0088271 | A1 | 4/2007 | Richards | |
| 2009/0163860 | A1* | 6/2009 | Patrick | A61B 8/00 |
| | | | | 604/83 |
| 2009/0198215 | A1* | 8/2009 | Chong | A61M 5/1413 |
| | | | | 604/506 |
| 2012/0136316 | A1* | 5/2012 | Davies | A61M 5/2448 |
| | | | | 604/191 |
| 2013/0253430 | A1 | 9/2013 | Kouyoumjian et al. | |
| 2013/0267908 | A1* | 10/2013 | Leak | A61M 5/31563 |
| | | | | 604/191 |
| 2016/0144101 | A1 | 5/2016 | Pananen | |
| 2016/0213849 | A1* | 7/2016 | Holtwick | A61M 5/24 |
| 2016/0235910 | A1* | 8/2016 | Damiano | A61M 5/16831 |
| 2019/0175819 | A1* | 6/2019 | Yang | A61M 5/162 |
| 2021/0030949 | A1* | 2/2021 | Damiano | A61M 5/142 |

FOREIGN PATENT DOCUMENTS

| | | |
|---|---|---|
| WO | 2007/108987 A2 | 9/2007 |
| WO | 2013/016376 A2 | 1/2013 |

OTHER PUBLICATIONS

International Search Report of PCT/FR2018/050375 dated May 4, 2018.

* cited by examiner

AUTOMATIC FLUID PRODUCT INJECTION DEVICE

CROSS REFERENCE TO RELATED APPLICATIONS

This application is a National Stage of International Application No. PCT/FR2018/050375 filed Feb. 16, 2018, claiming priority based on French Patent Application No. 1751321 filed Feb. 20, 2017.

The present invention relates to an automatic fluid injection device.

Automatic fluid injection devices are well known. In particular, they include autoinjectors in which the contents of a reservoir, generally a syringe, are automatically injected by means of an actuator system that generally includes a loaded spring, and that, on being triggering, moves a piston in the reservoir so as to inject the fluid.

Such prior-art devices can present problems, in particular when the volumes to be dispensed are large, when the fluid is relatively viscous, or when a plurality of fluids need to be combined in a single treatment.

Documents EP 2 179 754 and US 2007/088271 describe prior-art devices.

An object of the present invention is to provide an automatic injection device that does not have the above-mentioned drawbacks.

Another object of the present invention is to provide an automatic injection device that makes it possible to dispense fluid automatically, even at large volumes and/or high viscosities.

Another object of the present invention is to provide an automatic fluid injection device that is simple and inexpensive to manufacture and to assemble.

The present invention thus provides an automatic fluid injection device comprising: a base body for coming into contact with an injection zone; a support assembly for supporting an actuator mechanism that is controlled by power supply means; at least one fluid reservoir, each containing an injection piston, arranged in said base body; a needle assembly comprising an insertion actuator, needle movement means, a priming needle for associating with each reservoir and for penetrating into said reservoir before moving its piston, and an injection needle for penetrating into the injection zone and for injecting the contents of said reservoir(s) into said injection zone, said device including at least one actuator button for priming, inserting the injection needle into the injection zone, administering fluid, and then retracting the injection needle.

Advantageously, said base body includes a sticker for fastening onto the injection zone.

Advantageously, said base body includes at least two reservoirs, in particular three reservoirs.

Advantageously, the fluids contained in said reservoirs are dispensed simultaneously, being mixed together upstream of said injection needle.

In an advantageous variant, the fluids contained in said reservoirs are dispensed successively.

Advantageously, a respective actuator button is associated with each reservoir.

In an advantageous variant, the device includes a single actuator button.

Advantageously, for each reservoir, the actuator mechanism includes a cylinder containing a driving fluid, such as a saline solution, in which cylinder there may slide a respective plunger that is controlled by a drive mechanism.

Advantageously, said drive mechanism comprises an electric motor associated with a worm gear or with a clockmaker-type gear train.

Advantageously, said insertion actuator, advantageously an electromechanical actuator, such as a solenoid, is actuated after at least one of said reservoirs has been primed by said priming needles, said insertion actuator being connected to said injection needle by means of one or more pivot arms, so as to cause said injection needle to penetrate into said injection zone.

Advantageously, said insertion actuator is actuated after the contents of all of the reservoirs have been dispensed, so as to retract said injection needle from said injection zone.

Advantageously, each reservoir has a fluid content in the range 1 milliliter (mL) to 10 mL, advantageously about 3 mL.

Advantageously, said power supply means comprise an optionally rechargeable battery.

These characteristics and advantages and others appear more clearly from the following detailed description, given by way of non-limiting example, and with reference to the accompanying drawings, in which.

The invention relates to an automatic injection device that is particularly adapted to dispense relatively large volumes of fluid, typically about a few milliliters, typically in the range 1 mL to 10 mL, e.g. 3 mL. The device of the invention is also adapted to dispense fluids that are relatively viscous.

The device is preferably disposable and can operate with the following operating steps:

1) the user removes the packaging and fastens the device on an injection zone, e.g. by means of a sticker provided for this purpose;

2) the user presses on an actuator button 200 so as to actuate the device, which serves in particular to prime the device, to insert the injection needle into the injection zone, to administer the fluid, and then to retract the injection needle;

3) the user is alerted when the process has ended, and detaches the appliance from the body and disposes of it.

Figure 1:
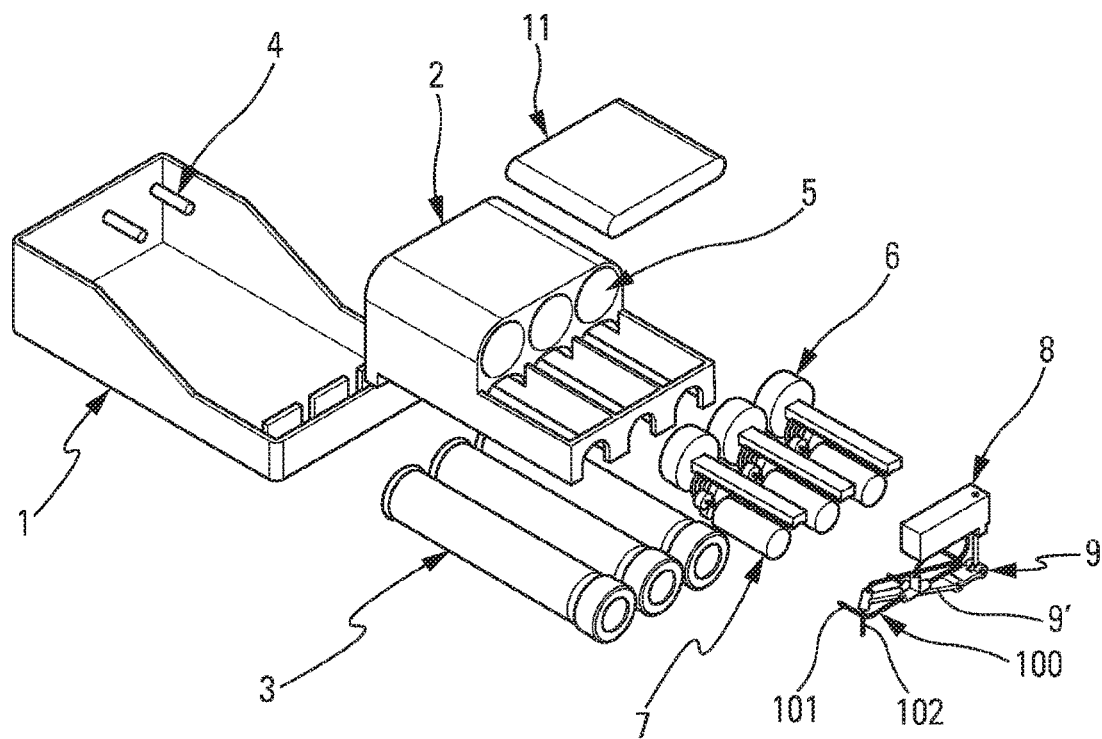
FIG. 1 is an exploded diagrammatic perspective view of an automatic injection device in an advantageous embodiment.
Figure 2:
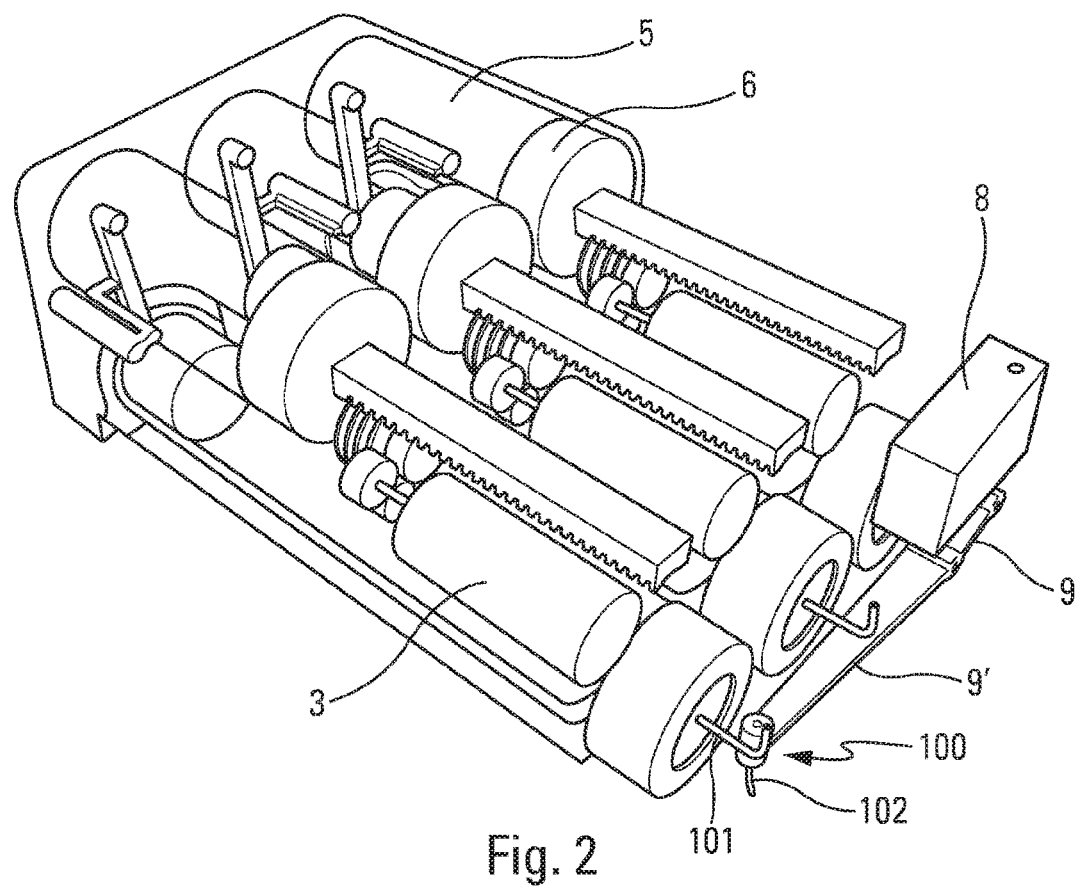
FIG. 2 is a diagrammatic perspective view of the inside of the FIG. 1 device.
Figure 3:
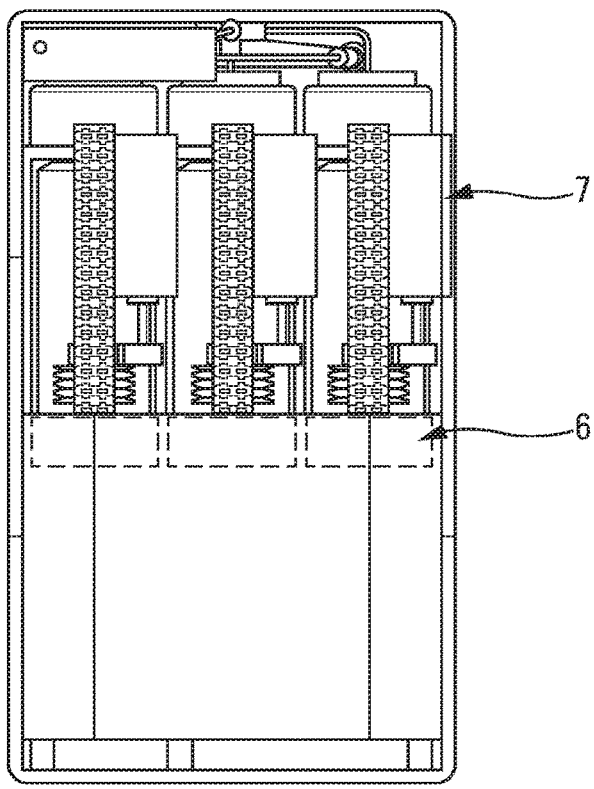
FIGS. 3 and 4 are diagrammatic plan views of two different variant embodiments of the actuator means of the device in FIGS. 1 and 2.

FIGS. 1 and 2 show an automatic injection device in a first advantageous embodiment.

The device comprises: a base body 1 for coming into contact with the injection zone; a support assembly 2 for supporting an actuator mechanism 5, 6, 7; one or more fluid reservoirs 3, each containing an injection piston 35, arranged in said base body 1; a needle assembly 100 comprising an insertion actuator 8, needle movement means 9, 9', one or more priming needles 101 for penetrating into the reservoir(s) 3, and an injection needle 102 for penetrating into the injection zone; and power supply means 11.

In the embodiment shown, the power supply 11 is an optionally rechargeable battery.

Figure 4:
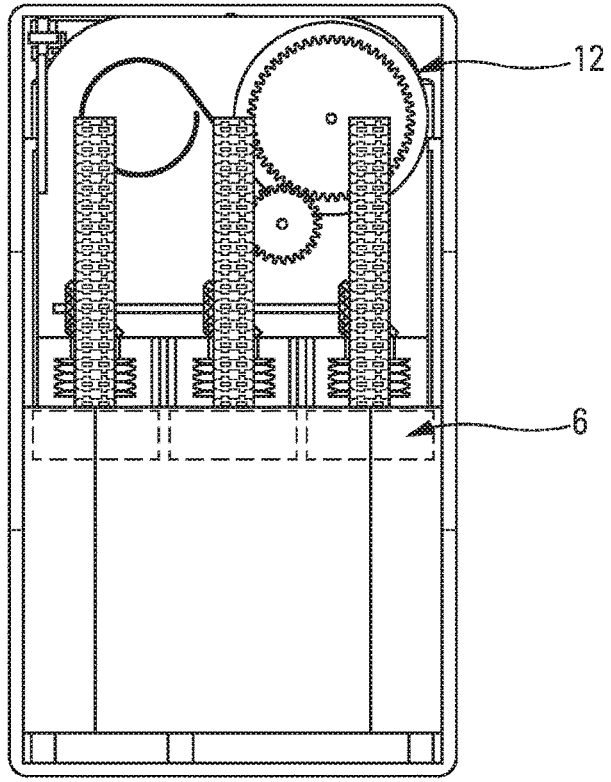
Figure 5:
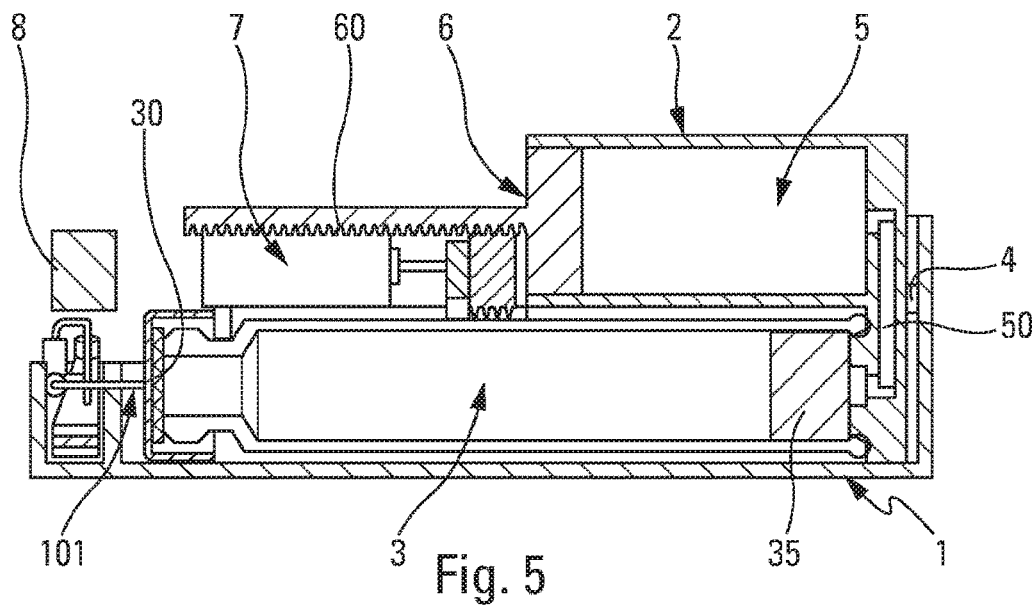
FIGS. 5 to 7 are diagrammatic side views of the actuation sequence of the device in FIGS. 1 and 2.
Figure 6:
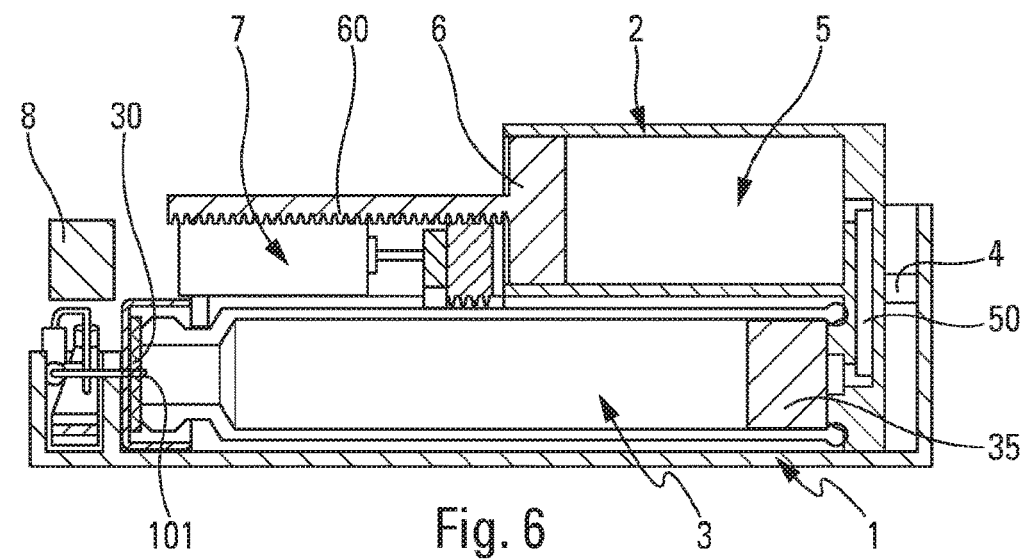
Figure 7:
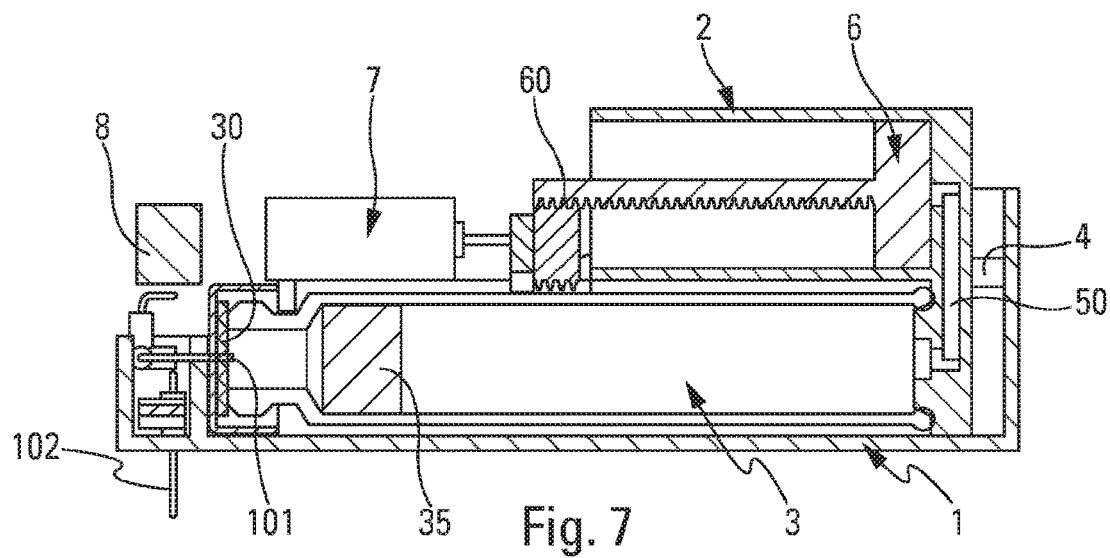
Figure 8:
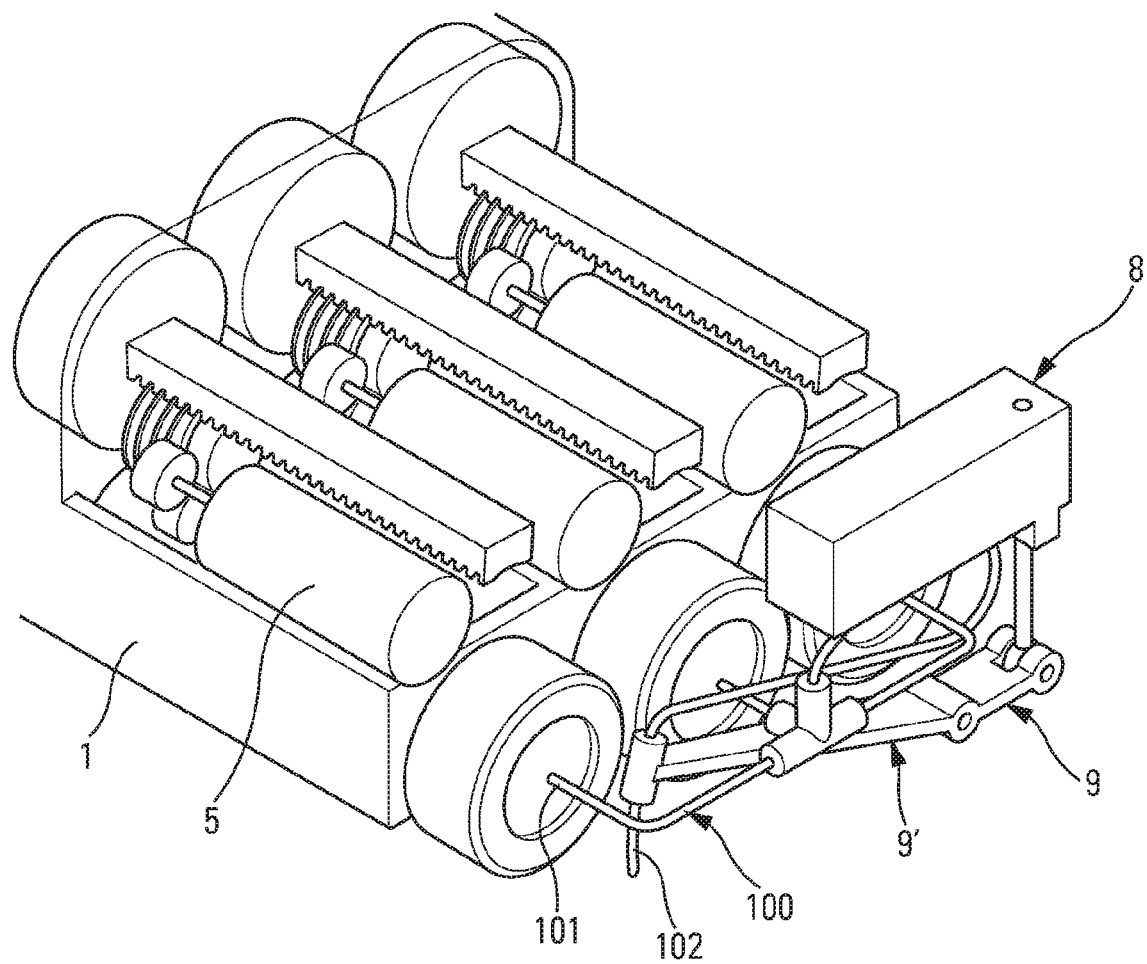
FIG. 8 is a diagrammatic and fragmentary perspective view of the needle assembly, before pricking.
Figure 9:
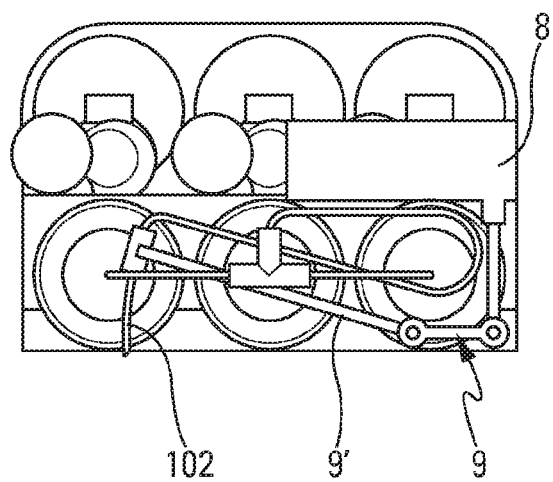
FIGS. 9 and 10 are diagrammatic side views of the needle assembly, respectively before and after pricking.
Figure 10:
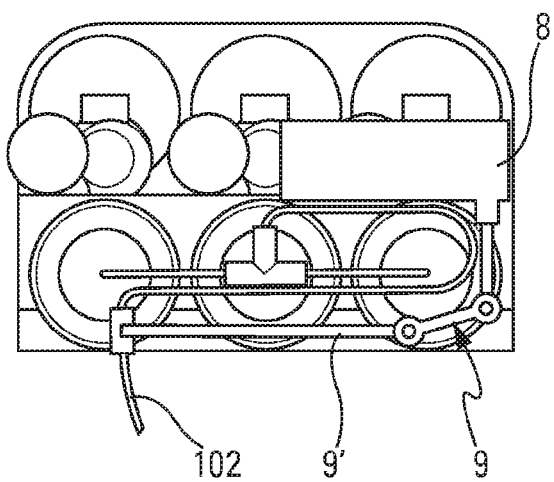
Figure 11:
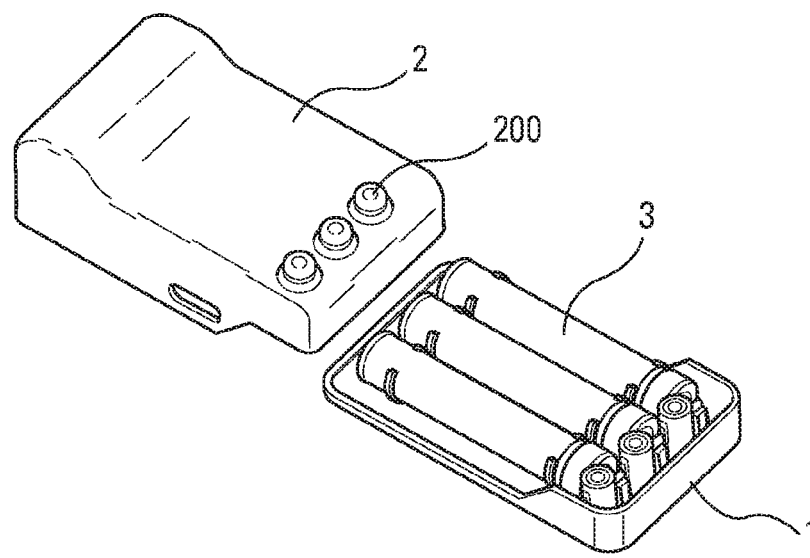
FIGS. 11 to 13 are diagrammatic perspective views of various variant embodiments.

In this embodiment, the actuator mechanism is of the hydraulic type, with at least one cylinder 5 containing a driving fluid, such as a saline solution, in which cylinder there may slide a respective plunger 6 that is controlled by a drive mechanism 7. After actuating the actuator button 200, the power supply 11 drives the plunger 6 to move linearly so as to compress a driving fluid contained in the cylinder 5. The plunger 6 may be moved by various known methods, including an electric motor associated with a worm gear 7, as shown in FIGS. 1 to 3 and 5 to 8, or with a clockmaker-type gear train 12, as shown in FIG. 4. In variants, it is possible to use actuator mechanisms other than hydraulic, e.g. mechanical, pneumatic, thermal, or chemical.

Advantageously, before actuation, the reservoir(s) 3 is/are closed by a septum-forming membrane 30, for piercing by a priming needle 101 during actuation. To this end, the device includes one or more priming pistons 4 for moving said support assembly 2 relative to said base body 1 at the start of actuation, so as to perform priming by piercing the membrane(s) 30.

Advantageously, the needle movement means 9 comprise one or more hinged arms 9, 9' supporting the injection needle 102 and controlled by the insertion actuator 8. The insertion actuator 8 may be an electromechanical actuator, such as a solenoid.

In the above-described device, the operations of piercing the septum and of dispensing the fluid are both actuated by the same actuator cylinder 5. The actuator cylinder 5, the plunger 6, the drive mechanism 7, and the reservoir 3 are all secured to the support assembly 2. The support assembly can slide relative to the base body 1 that is fastened to the patient. The needle assembly 100 is stationary relative to the base body 1.

During actuation, the drive mechanism 7 of the plunger 6 causes the plunger 6 to extend, and this moves the hydraulic fluid. This causes the priming piston(s) 4 to extend, thereby moving the entire support assembly 2, including the reservoirs 3, relative to the base body 1. The reservoirs 3 are forced against the needle assembly 100, piercing the septums by means of the priming needles 101. The device is now primed.

After the device has been primed, the injection needle 102 is inserted into the injection zone of the patient by means of an insertion actuator 8, advantageously an electromechanical actuator, such as a solenoid. The actuator 8 is connected to the injection needle 102 by means of one or more pivot arms 9, 9'.

When a plurality of cartridges are used, as shown in the example in FIGS. 1 and 2, the priming needles 101 of all of the reservoirs 3 are coupled to a single injection needle 102.

At rest, the actuator 8 is in its deployed position. The needle assembly 100 and the pivot arms 9, 9' are in their retracted positions.

The injection needle 102 is deployed once the device has reached its primed state. By way of example, this may be determined by means of a mechanical and/or software controller, e.g. once the priming piston(s) 4 is/are fully extended. When it is deployed, the actuator 8 retracts, and this causes the pivot arms 9, 9' to move the injection needle 102 into the injection zone. The injection needle 102 is advantageously curved so that it can flex, so as to enable the tip of the needle to move. The curved shape is also advantageous for adapting to the pivot movement of the pivot arms 9, 9'.

After inserting the injection needle, the drive mechanism 7 continues to extend the plunger 6. This moves more hydraulic fluid through a channel 50 of the support assembly 2, to the rear of the reservoir 3, and this drives the piston 35 of the reservoir towards the front and delivers the fluid. The force required for this operation is greater than the force required to drive the priming pistons 4, so as to guarantee that priming occurs first.

Once sufficient fluid has been injected, the process is terminated by stopping the operation of the drive mechanism 7.

Once dispensing of the fluid has terminated, the insertion actuator 8 retracts the needle into the device. The end of dispensing of the fluid can be identified by a mechanical and/or software inspection, e.g. once the drive mechanism 7 is fully extended.

The above-described embodiment provides the following advantages in particular:
  the septum is pierced and medication is delivered by the same mechanism, minimizing the number of components;
  the flow of fluid is controlled accurately;
  its shape is compact;
  the tip of the injection needle is curved so as to minimize discomfort of the patient during the injection process; and
  the path of the fluid is simple, and this minimizes any risk of contamination.

The embodiment shown in FIGS. 1 and 2 shows a device that is adapted to include one, two, or three reservoirs 3. Provision may be made to use masks on the needle assembly, which masks are perforated/penetrated by the presence of the reservoir, during priming of the device. When a reservoir is not present, its mask acts to seal the respective branch of the needle assembly, preventing medication from leaking during dispensing.

The device shown in FIGS. 1 and 2 includes three drive mechanisms 7 that act on three reservoirs 3. The three drive mechanisms 7 may be actuated simultaneously by means of a single actuator button 200 so as to dispense the contents of the three reservoirs simultaneously, which contents are thus mixed together upstream of the injection needle 102. In a variant, the three drive mechanisms 7 may be actuated successively so as to dispense the contents of the three reservoirs successively. The successive actuations may be triggered by means of three separate actuator buttons 200, but provision could also be made for a single actuator button 200 that automatically triggers the dispensing sequence. A combination of these two variants is also possible, e.g. dispensing in two stages, i.e. firstly dispensing the contents of one reservoir, and secondly simultaneously dispensing a mixture from the other two reservoirs.

The above-described embodiment provides the following advantages in particular:
  the speed of dispensing the fluid may be adjusted so as to optimize individual treatments, and it may also vary over time; and
  the drive mechanisms and the multiple reservoirs make it possible to use a combination of medications that may be dispensed at different speeds and at different moments.

The use of a device having one or more reservoirs makes it possible in particular to provide the following advantages:
  a single device for two or more types of fluid, which may require different volumes to be dispensed;
  the possibility of dispensing cocktails or a mixture of two or more fluids;

the possibility of associating pain-reducing agents (anesthetics, acid neutralizers, etc.) with the medication to be injected;

the possibility of having different medication treatment frequencies; e.g. a first sequence S1 of taking a plurality of different medications, followed by a second sequence S2 of taking a single medication, etc.;

the possibility of standardizing the injection device for several types of treatment;

a reduction in the cost of developing devices;

the possibility of adjusting the formulation of the fluid;

various fluid formulations may be housed in a single device; and a reduction in the number of injections.

Figure 12:
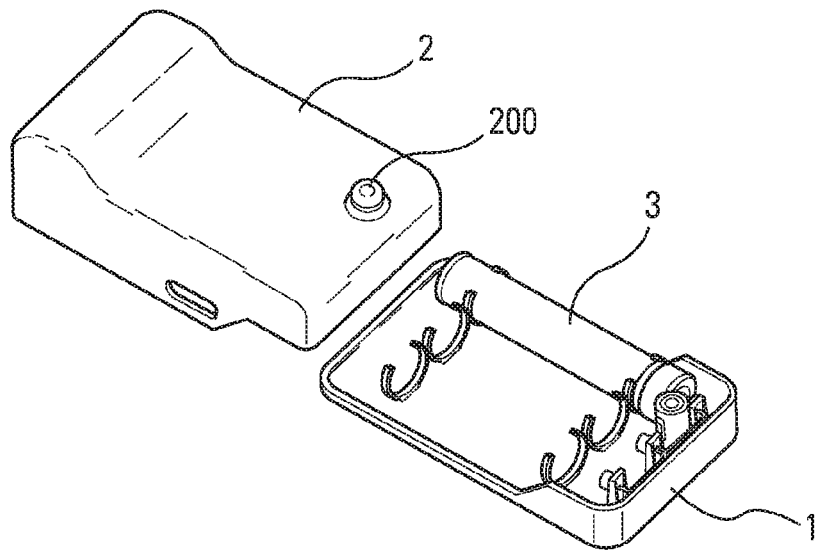
Figure 13:
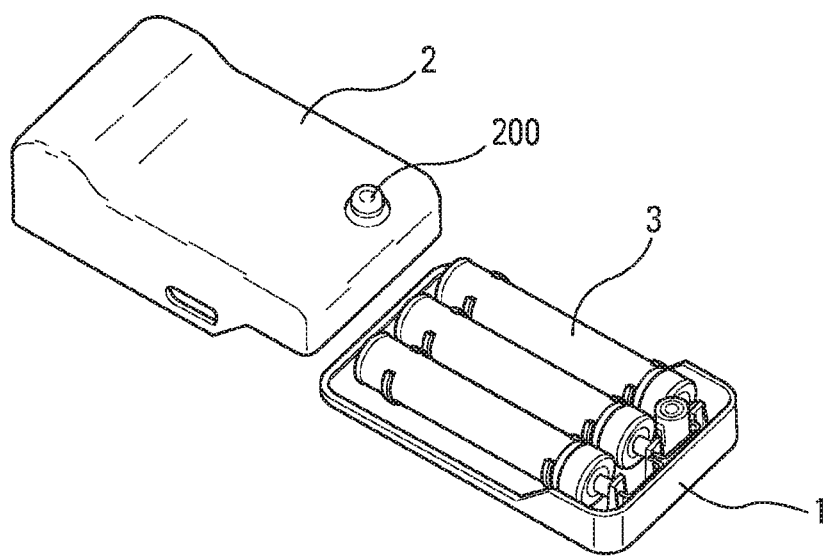

Other configurations are possible, for example:

a single drive mechanism 7 actuating a single reservoir (FIG. 12); and a single drive mechanism 7 actuating a plurality of reservoirs simultaneously, in particular three reservoirs (FIG. 13).

It is also possible to envisage using multiple needle assemblies in a single device, with independent control both of needle insertion and of fluid injection. This would enable:

sequential dispensing of the fluid for a reduced flowrate;

the reduction in the size of the injection needle so as to increase the flowrate of the fluid and reduce the pain of the patient; and the diameter of the injection needle to be optimized for a given formulation of medication, when various medications are contained in the same device.

The use of simultaneous or sequential injections may be applied in a system having a plurality of cartridges in order to:

reduce the flowrate of fluid and ease the pain of the patient; and make it possible to improve the effectiveness of certain preparations of cocktails of medications.

The present invention is described above with reference to advantageous embodiments and variants, but naturally any modification could be applied thereto by a person skilled in the art, without going beyond the ambit of the present invention, as defined by the accompanying claims.

The invention claimed is:

1. An automatic fluid injection device comprising: a base body for coming into contact with an injection zone; a support assembly supporting an actuator mechanism that is controlled by power supply means; at least one fluid reservoir, each containing an injection piston, arranged in said base body; a needle assembly comprising an insertion actuator, needle movement means, a priming needle for associating with each reservoir and for penetrating into said reservoir before moving its piston, and an injection needle for penetrating into the injection zone and for injecting the contents of said reservoir(s) into said injection zone, said device including at least one actuator button for priming, inserting the injection needle into the injection zone, administering fluid, and then retracting the injection needle.

2. A device according to claim 1, wherein said base body includes a sticker for fastening onto the injection zone.

3. A device according to claim 1, wherein said base body includes at least two reservoirs.

4. A device according to claim 3, wherein the injection pistons of said reservoirs are configured to dispense the fluid within said reservoirs simultaneously.

5. A device according to claim 3, wherein the injection pistons of said reservoirs are configured to dispense the fluid within said reservoirs successively.

6. A device according to claim 1, wherein a respective actuator button is associated with each reservoir.

7. A device according to claim 1, including a single actuator button.

8. A device according to claim 1, wherein, for each reservoir, the actuator mechanism includes a cylinder containing a driving fluid, and wherein a respective plunger is provided to slide within the cylinder and is controlled by a drive mechanism.

9. A device according to claim 8, wherein said drive mechanism comprises an electric motor associated with a worm gear or with a clockmaker-type gear train.

10. A device according to claim 8, wherein the driving fluid is a saline solution.

11. A device according to claim 1, including electromechanical means for actuating said insertion actuator after at least one of said reservoirs has been primed by said priming needles, said insertion actuator being connected to said injection needle by one or more pivot arms, so as to cause said injection needle to penetrate into said injection zone.

12. A device according to claim 11, including electromechanical means for actuating said insertion actuator after the contents of all of the reservoirs have been dispensed, so as to retract said injection needle from said injection zone.

13. A device according to claim 11, wherein the electromechanical means for actuating the insertion actuator is an electromechanical actuator.

14. A device according to claim 13, wherein the electromechanical means for actuating the insertion actuator is a solenoid.

15. A device according to claim 1, wherein each reservoir has a fluid content in the range 1 mL to 10 mL.

16. A device according to claim 15, wherein each reservoir has a fluid content of about 3 mL.

17. A device according to claim 1, wherein said power supply means comprise a rechargeable battery.

18. A device according to claim 1, wherein said base body includes three reservoirs.

* * * * *